United States Patent [19]

de Loos-Vollebregt et al.

[11] Patent Number: 5,218,553
[45] Date of Patent: Jun. 8, 1993

[54] METHOD FOR DETERMINING CONCENTRATIONS BY MEANS OF ATOMIC EMISSION SPECTROSCOPY

[75] Inventors: M. T. C. de Loos-Vollebregt, Pijnacker; E. H. van Veen, MR Leiden, both of Netherlands

[73] Assignee: The Perkin-Elmer Corporation, Norwalk, Conn.

[21] Appl. No.: 569,888

[22] Filed: Aug. 20, 1990

[30] Foreign Application Priority Data

Aug. 23, 1989 [DE] Fed. Rep. of Germany ....... 3927768

[51] Int. Cl.$^5$ .............................................. G06F 15/20
[52] U.S. Cl. ..................................... 364/498; 356/326
[58] Field of Search ............... 356/305, 319, 326, 328; 364/497, 498

[56] References Cited

U.S. PATENT DOCUMENTS

| | | | |
|---|---|---|---|
| 3,637,310 | 1/1972 | Naono | 356/319 X |
| 3,734,621 | 5/1973 | Moody et al. | 356/325 |
| 3,955,891 | 5/1976 | Knight et al. | 356/330 X |
| 4,636,074 | 1/1987 | Levy et al. | 356/328 |
| 5,087,123 | 2/1992 | Gerlacher et al. | 356/307 |

FOREIGN PATENT DOCUMENTS

| | | |
|---|---|---|
| 3131111 | 2/1983 | Fed. Rep. of Germany . |
| 3418081 | 11/1985 | Fed. Rep. of Germany . |
| 3701583 | 8/1988 | Fed. Rep. of Germany . |
| 3720977 | 1/1989 | Fed. Rep. of Germany . |

OTHER PUBLICATIONS

Brown; "The Kalman Filter in Analytical Chemistry"; *Analytica Chimica Acta*, 181 (Mar. 1986) pp. 1-26.
*Journal of Chemometrics*, Band 3, 1988, John Wiley & Sons Ltd. Gail Hartmann Webster et al. "Characterization of the effect of peak shifts on the performance of the Kalman Filter in multi-component analysis" Seiten 21-32.
*Spectrochimica Acta*, Teil B: Atomic Spectroscopy; Band 42B, Nr. 6, 1987, Pergamon Press; Oxford, New York P. W. J. M. Boumans et al. "Detection limit including selectivity as a criterion for line selection in trace analysis using inductively coupled plasmaatomic emission spectrometry (ICP-AES)-a tutorial treatment of a fundamental problem of AES" Seiten 819-840.
*Analytical Chemistry*, Band 53, 1981, American Chemical Society T. F. Brown et al. "Resolution of overlapped Electrochemical Peaks with the Use of the Kalman Filter" Seiten 1410-1417.
*Analytical Letters*, Teil B.-Clinical and Biochemical Analysis, Band 13(A14), Nr. B10, 1980 H. N. J. Poulisse et al. "The Kalman Filters as an On-Line Drift Compensator in Multi-component Analysis Determinations" Seiten 1211-1234.

*Primary Examiner*—Edward R. Cosimano
*Attorney, Agent, or Firm*—Edwin T. Grimes

[57] ABSTRACT

A method for determining concentrations by means of atomic emission spectroscopy which contains the method steps: (a) generating an atomic emission with a known concentration of a looked-for element, (b) scanning the obtained emission spectrum by means of a spectral photometer with a spectral slit width in a wavelength range which contains a spectral line of the looked-for element, (c) generating an atomic emission with an unknown sample which contains the looked-for element with the concentration of the looked-for element in the unknown sample to be determined, (d) scanning the obtained emission spectrum by means of the spectral photometer with the same spectral slit width and in the same wavelength range in which the scanning of the emission spectrum with the known concentration was made, (e) processing the spectral-representing signal, which is provided by the spectral photometer independent of the wavelength by means of a recursive Kalman filter, in order to generate an estimate for the concentration of the looked-for element.

4 Claims, 7 Drawing Sheets

METHOD FOR DETERMINING CONCENTRATIONS BY MEANS OF ATOMIC EMISSION SPECTROSCOPY

TECHNICAL FIELD

The invention relates to a method for determining concentrations by means of atomic emission spectroscopy.

BACKGROUND ART

Elements which are present in atomic state emit, when they are excited, the line spectrum of the atoms. Depending on the nature of the excitation by means of an inductively coupled plasma, there are also observed from many elements the emission spectra originating from ions, i.e. ionized atoms. For reasons of simplicity, reference will be made hereinafter to atomic spectra which term will be understood to encompass the emission spectra of atoms as well as ions. Each element provides a line spectrum which is characteristic of this element. In such a line spectrum there are strong spectral lines, i.e. spectral lines having a high intensity, and less strong or weaker spectral lines. The intensity of the spectrum depends on the number of excited atoms in the light source. The spectral lines are very narrow and have a width of a few picometers.

It is known to introduce a sample solution which is to be analyzed into a plasma heated by high frequency and, for determining the concentration, to measure the intensities of certain spectral lines which are characteristic of different looked-for elements. A light beam originating from the plasma is spectrally dispersed by a spectrometer by means of a monochromator and the light intensity is measured as a function of wavelength using light-sensitive detector means. The detector means produce signals at the aforementioned characteristic spectral lines originating from the various looked-for elements. After corresponding calibration, the concentration of the individual elements can be determined from these signals.

In addition to the spectral lines of the different elements, there occurs a non-specific background emission. This background emission can depend on the wavelengths and can be structured.

In some cases, the spectral lines of different elements overlap. It is then difficult to determine the concentrations of such overlapping spectral lines.

In a publication by S. D. Brown "The Kalman Filter in "Analytical Chemistry" from "Analytica Chimica Acta", 181 (1986), 1-26 it is known to use Kalman filters for separating the overlapping signals of analyzing apparatus or for the drift compensation. It is mentioned that the condition variables can also be dependent on the wavelength instead of on the time. Algorithms used in the recursive, discrete Kalman filter are also described. In every recursion step an estimate of the condition vector is described. In the subsequent recursion step, a vector of a measurable variable or variables is measured. From a measuring matrix it is calculated which vector of measurable values, according to the estimate determined in the preceding recursion step, is to be predicted. The estimate of the condition vector is corrected by the difference between the measurable variables and the predicted measurable variables multiplied by a filter amplification. In this publication the possibility is also pointed out that the measuring matrix consists of several column vectors, each of which is a complete, visible spectrum as a consequence of molar absorption abilities. This measuring matrix interrelates the absorbency values measured with different wavelengths and the conditions of the filter, which can be stated as concentrations of the components. The filter model which is used is made from experimentally obtained signals from the analyzing apparatus. A filter with such empiric signals can serve for the easy resolution of overlapping spectra, i.e. absorption spectra.

A publication by T. F. Brown and S. D. Brown "Resolution of Overlapped Electrochemical Peaks with the Use of the Kalman Filter" in Analytical Chemistry" vol. 53 (1981), 1410–1417, describes the separation of overlapping electrochemical peaks by means of the Kalman filter. Also, curves with standard solutions of different elements are recorded. From these curves a model for a Kalman filter is formed. In this publication there is also described an innovation sequence as well as the displacement between sample spectra and model spectra by means of an iterative procedure.

A publication by G. H. Webster, T. L. Cecil and S. C. Rutan "Characterization of the Effect of Peak Shifts on the Performance of the Kalman Filter in Multicomponent Analysis" in "Journal of Chemometrics" vol. 3 (1988), 21–32 describes fluorescence analysis. However, in fluorescence analysis, problems occur in that the fluorophores are sensitive to the polarity of the vicinity. Thereby a spectral shift of the fluorescence emission spectrum by some nanometers can be effected. This publication also contains an indication of the magnitude of the covariance P and the variance of the noise in the measurement ($S_x^2$).

Also in this publication, the Kalman filter serves for the separation of overlapping spectra. The publication concerns the influence of peak shifts on the performance of the algorithms of a multi-component analysis with a Kalman filter. It is shown that the course of the difference between the actually measured measurable variable and the measurable variable predicted by the filter provides a measure for the amount and direction of the peak shift.

A publication of H. N. J. Poulisse and P. Engelen "The Kalman Filters as an On-line Drift Compensator in Multicomponent Analysis Determinations" in "*Analytical Letters*" 13(A14) (1980), 1211–1234 describes the compensation of a baseline drift in an analyzing apparatus by means of the Kalman filter. In the condition vector which is substantially formed by two concentrations, two different elements are provided with one being a factor multiplied by the running number and the other one being a constant. These two values are drift parameters which are provided by the Kalman filter.

SUMMARY OF THE INVENTION

It is an object of the invention to reduce the detection limits in atomic absorption spectroscopy, particularly in ICP-AES and in optical emission spectroscopy ICP-OES.

Further, the possibility of separating overlapping lines and of detecting background emission is provided.

According to the invention these and other objects are achieved by a method comprising the steps of:

(a) generating an atomic emission with a known concentration of a looked-for element, (b) scanning the obtained emission spectrum by means of a spectral photometer with a spectal slit width in a wavelength range which contains a spectral line of the looked-for element, (c) generating an atomic emission with an unknown sample which contains the looked-for element, with the concentration of the looked-for element in the unknown sample to be determined, (d) scanning the obtained emission spectrum by means of the spectral photometer with the same spectral slit width and in the same wavelength range in which the scanning of the emission spectrum with the known concentration was made.

(e) processing the spectrum-representing signal, which is provided by the spectral photometer independent of the wavelength by means of a recursive Kalman filter, in order to generate an estimate of the concentration of the looked-for element.

Heretofore, in atomic emission spectroscopy, each of the individual spectral lines was detected by a detector associated with a spectrometer. According to the present invention, the spectral lines are scanned by a spectral photometer. This scan is made for one solution of an individual, looked-for element as well as for several solutions, each of which contains an individual element in a known concentration, and for a sample which is to be analyzed. This scan is made with a finite spectal slit width. Thereby, of course, the accurate intensity course of the very narrow spectral lines cannot be determined. However, no harm is done when the scanning in the "model" and in the actual sample is made with the same spectral slit width. The thus obtained "model" of the spectrum with the concentrations as parameters serves for constructing a Kalman filter which determines, with a technique which is known, the concentrations from the intensity courses obtained with the sample. As a result of such scanning of the line spectrum, a considerable diminution of the detection limit can be achieved.

The recursive Kalman filter can: consecutively detect, with the recursion steps in wavelength steps, the signals of the spectral photometer; form the difference (innovation) of each measured signal from a predicted signal which results from the estimate of the concentration obtained in the preceding recursion step; and correct the estimate of the concenataon by this difference (innovation) multiplied by a filter amplification in order to form a new estimate for the subsequent recursion step.

The width of the spectral lines obtained with atomic absorption spectroscopy is in the range of picometers. Therefore, the problem results that, with the scanning of the spectral lines of standard solution(s) and with the scanning of the spectral lines of the sample, the wavelenth scales can be shifted with respect to each other by negligible changes at the spectral photometer.

These problems can be resolved because the wavelength values associated with the signals obtained with scanning the emission spectrum of the known concentrations and the wavelength values associated with the signals obtained with scanning the emission spectrum of the sample, are displaced relative to each other by means of an iterative procedure until the innovation, i.e. the difference between the measured and the predicted intensity as a function of the wavelength, has a flat course.

Emission spectra of a plurality of looked-for elements having a known concentration can be individually generated, the emission spectra can be scanned with said spectral slit width by means of the spectral photometer, and a model of the emission spectrum of the sample can be formed from the thus obtained emission spectra which are normalized with respect to the concentrations. During such operation, displacement may occur between the emission spectrum relative to emission spectra which are known from the literature, due to, for example, instabilities present in the spectral photometer. This problem is eliminated by means of the Kalman filter using the aforementioned iterative procedure. When carrying out this procedure, the wavelength values of the model emission spectrum and the wavelength values of the emission spectrum known from the literature are varied relative to each other within a predetermined wavelength range until an optimum innovation is obtained, i.e. the difference in the intensities of the model and the literature spectrum has a flat course as a function of the wavelength. The Kalman filter can form concentration estimates on the basis of the model. Also the spectral lines of the looked-for elements may overlap with the scanned wavelength range.

Further, it is possible that the model on which the Kalman filter is based allows for background emission.

Embodiments of the invention will now be described in greater detail with reference to the accompanying drawings.

PREFERRED EMBODIMENT OF THE INVENTION

The Kalman filter causes recursive, digital signal-processing which allows for estimates of concentrations of elements in samples from noisy measurements on emission spectral lines. It is focussed on a scan of a spectral window containing overlapping spectral lines, whereby the scan is made in wavelength steps from a wavelength position $\lambda_1$ up to a wave length position $\lambda_n$. The wavelength $\lambda_k$ is the independent variable.

The system is modelled by two equations. The first equation describes the wavelength dependence of the system and contains the variables which are to be filtered or estimated in a condition vector. In the present case of determining the concentration, the condition vector $C(\lambda_k)$ is a vector, the components of which are the concentrations of the looked-for elements in the sample. Since these concentrations are constant and do not depend on the wavelengths, the "system equation" of the Kalman filter is:

$$C(\lambda_k) = I\, C(\lambda_{k-1}) \qquad (1)$$

where:

I denotes the identity matrix. The measuring equation is:

$$x(\lambda_k) = S^T(\lambda_k)\, C(\lambda_k) + v(\lambda_k) \qquad (2)$$

where:

$x(\lambda_k)$ denotes the signal of the spectrometer obtained with the wavelength position $\lambda_k$. "$S^T$" is a slit vector and $S^T$ is the associated transposed vector, i.e. a line vector. The vector S relates the components of the condition vector C, i.e. the concentrations of the different elements in the sample, to the measured signal. "v" designates the measuring noise.

The measuring equation generally relates the conditions summarized in the condition vector to the measured "measureable variables". In the present case, this is made by the vector S. The vectors $S(\lambda_k)$ for the different values of k (k=1 ... n) form a matrix S. Each column vector $S(\lambda_k)$ represents the sensitivity of the spectral photometer for the different elements with the wavelength position k. These column vectors S are experimentally determined. For the respective elements the spectra within the spectral window are separately scanned. The signals obtained for the different wavelength positions k are divided by the known concentrations in which the element was present for this scan. In practice this amounts to the making of calibration curves.

The thus obtained vectors represent "experimental models". The vectors contain noise which is not smoothed and can be incorporated into the noise term v.

Furthermore, structured background emission including the background emission caused by the solvent is modelled in the matrix S. In a Kalman filter, also, other kinds of background emission can be considered. Therefore, it is assumed that the background emission shows at most a parabolic course. Thus, the matrix S is enlarged by three column vectors containing elements proportional to "1", or "$\lambda_k$" or "$\lambda_k^2$". When during the signal processing it turns out that the filtered coefficients of the linear and quadratic terms are very small, which is often the case, only the first of these column vectors is retained.

Thus, it is not required to effect a background compensation prior to the signal-processing by the Kalman filter.

The general algorithms according to (1) and (2) result in an extrapolation of the condition estimate in:

$$C(\lambda_k;\lambda_{k-1}) = C(\lambda_{k-1};\lambda_{k-1}) \qquad (3)$$

and an extrapolation of the error covariance in:

$$P(\lambda_k;\lambda_{k-1}) = P(\lambda_{k-1};\lambda_{k-1}) \qquad (4)$$

The Kalman amplification vector, i.e. the vector of the factors by which the differences between the measurable values and the predicted measurable value are multiplied to form a correcting term for the component of the condition vector, results in $$K(\lambda_k) = P(\lambda_k;\lambda_{k-1})S(\lambda_k)(S^T(\lambda_k)P(\lambda_k;\lambda_{k-1})S(\lambda_k)+v^2(\lambda_k))^{-1}. \qquad (5)$$

Therewith, the recursion equation by which a predicted estimatation value for the recursion step k is formed from the estimate of the recursion step (k − 1), becomes:

$$C(\lambda_k;\lambda_k) = C(\lambda_k;\lambda_{k-1}) + K(\lambda_k)(x(\lambda_k) - S^T(\lambda_k)C(\lambda_k;\lambda_{k-1})). \qquad (6)$$

The recursion formula for the error covariance becomes:

$$P(\lambda_k;\lambda_k) = (I - K(\lambda_k)S^T(\lambda_k))P(\lambda_k;\lambda_{K-1}) \qquad (7)$$

The equations (3) and (4) are calculated prior to the measurement in the wavelength position $k$ and provide the optimal, a priori estimate C and its error covariance matrix P. Then, a measurement in the wavelength position $\lambda_k$ is made. With the equations (5) to (7) the optimal, priori estimates are obtained. Thus, the new information from the measurement x is used for forming a correcting value which is added to the priori estimate. The inversive term in the Kalman amplification vector K is scalar. Therefore, no inversion of a matrix is required but only a division by a scalar.

Since the filter works inversively, initial values for $C(\lambda_0;\lambda_0)$ and $P(\lambda_0;\lambda_0)$ have to be estimated. For this purpose the concentrations and the off-diagonal covariances are set to zero. The diagonal covariances are set to a value which is larger than the variance $v^2(\lambda_k) = v^2$ in the measurement. It was found that an initial covariance should exceed 100 $v^2$. The estimates are only influenced by the ratio, not by the absolute values of the variance and the covariances. Therefore, it is assumed $P(_0; _0) = 10\ 000\ v^2$ and $v^2 = 1$. Then, the ratios for the initial conditions result in:

$$V^2(\lambda_k) = 1 \tag{8}$$

$$C(\lambda_0; \lambda_0) = 0 \tag{9}$$

$$P(\lambda_0; \lambda_0) = 10\ 000\ I \tag{10}$$

The equations (8) to (10) guarantee that the estimates of the concentrations do not depend on the estimated initial values. When the spectrum is scanned, the shape and the intensity of the signals of the spectral photometer remain stable over a sufficient period of time. However, to obtain unbiased estimates of the concentrations in the multi-component analysis, one substantial requirement has to be fulfilled: the wavelength divisions in the scans of the spectra for the experimental models and in the scan of the spectrum of the sample for the measurement should coincide. The shift of the wavelength divisions should be in the range of 0.1 picometer at most. Scanning spectral photometers do not fulfill these conditions. In such spectral photometers a wavelength adjusted at the monochromator can not be precisely maintained on a picometer over a longer period of time. The wavelength adjustment of monochromators depends on the position of mechanical elements. These are affected by external influences, e.g. by the ambient temperature.

Figure 1:
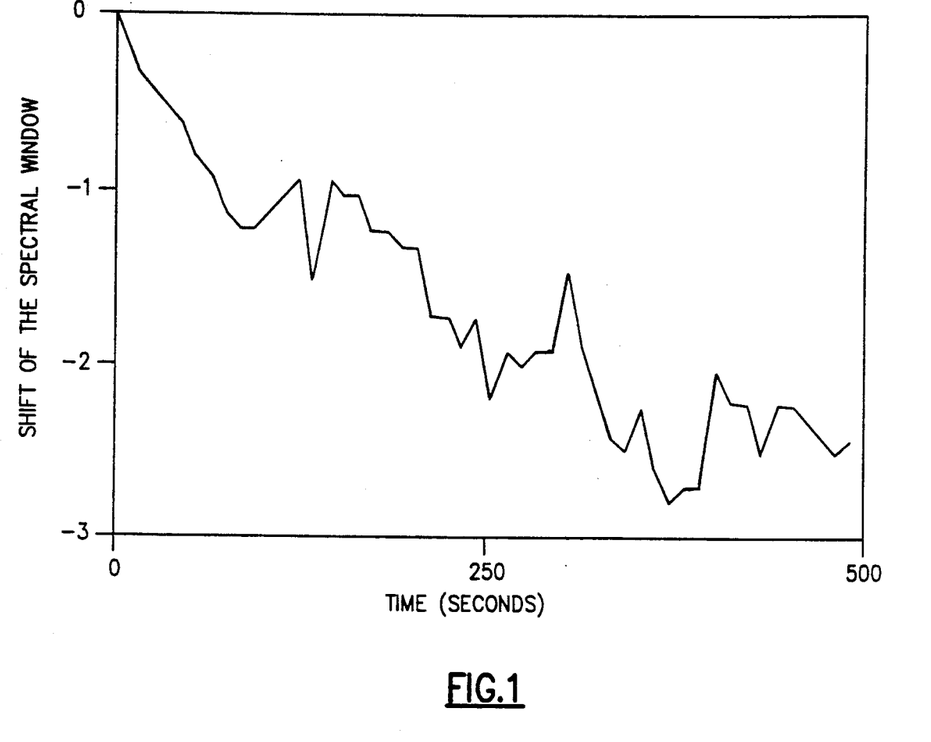
FIG. 1 shows the shift of the spectral window in the monochromator as a function of time.

FIG. 1 shows an example of the shift of the spectral window as a function of time in a monochromator used for measurements of the present type.

However, this problem can be solved by the Kalman filter. First the experimental models are measured. From this measurement the wavelength position of the peak maxima in the spectral window is calculated. Then, the wavelength scales of the single models are shifted relative to each other so as to give relative peak postions known from the literature. When the peak positions are not known or are not known with the required accuracy, they have to be determined during the further course of the method.

Now, a filtering of the measured values obtained with the sample is made by means of the Kalman filter. It is in no way clear with which wavelength positions the measured data have to be associated. The peak in the spectrum lies at any point between the peaks of the emission spectral lines of the components. With the filtering the course or the sequence of the "innovations" is calculated. The innovation is the difference between the actual measured value and the predicted estimate as it results from the estimate of the condition vector and the measuring matrix. The "innovation" is given by $$in(\lambda_k) = x(\lambda_k) - S^T(\lambda_k)C(\lambda_k; \lambda_{k-1}) \tag{11}$$

When the wavelength divisions of the spectra of the model and of the sample differ, marked structures come up in the course or in the sequence, respectively, of the innovations. When the wavelength divisions coincide the innovation as a function of the wavelength is a constant; it exhibits only white noise. Therefore, the course of the inovation is a criterion which allows the elimination of the problem of optical instability of the monochromator. The wavelength division of the spectrum of the sample is shifted relative to the wavelength division of the models in steps of 0.1 picometer. This is done until a constant innovation which is independent of the wavelength results. Then, unbiased values for the concentrations are obtained.

The innovation sequences define a characteristic inovation number $N_{in}$, which is determined by the summation according to equation (11a):

$$N_{in} = \frac{1}{n} \sum_{k=1}^{n} \tag{11a}$$

The characteristic innovation number $N_{in}$ assumes a minimum value whenever the aforementioned criterion is satisfied, i.e. the wavelength divisions of the model spectrum coincide with the wavelength division of the sample spectrum and the innovation is a constant as a function of wavelength. The minimum of the innovation number is preferably found by utilizing an interactive procedure based on successive interval halving steps. During such procedure, the measured values are displaced relative to the model vectors by interpolation and the innovation number $N_{in}$ is determined for each displacement by employing the Kalman filter. In detail, a displacement associated with the minimum innovation number $N_{in}$ and its immediately adjacent innovation numbers $N_{in}$ are selected. Upon halving of the intervals, there is carried out a further determination of the minimum innovation number $N_{in}$. This iteration is continued until the interval halving results in values below 0.1 picometer.

This kind of signal-processing sacrifices the capability of real-time data processing. However, the iteration takes less time. The equations (5) and (7) are calculated only once for a given matrix S prior to the iteration. Moreover, few steps are needed. The magnitude and the direction of the drift are almost known. The performance of the monochromator (FIG. 1) is rather constant during the day and from day to day.

If some structure still persists in the course of innovation, the relative wavelength position in the model may be false. This wavelength position can be optimized in the same way as described above, i.e. by an iterative search for a flat course of the innovations. Other reasons for a structure in the course of the innovations may be in the omission of the spectrum of a present element in the model. Conversely, when a spectrum of an element which is not present in the model is considered only zero concentration results.

The described Kalman filter can also deal with structured as well as unstructured background emissions.

The performance of the Kalman filter is characterized, among other things, by the detection limit. In the case of a dynamic measurement the detection limit in the presence of line overlap can be approximated by $$C_{L,true} = \frac{2x_I}{5S_A} + \frac{2\sqrt{2}\ sd_{BI}}{S_A} \tag{12}$$

where $x_I$ is the net interfering signal at the wavelength of the spectral line of the looked-for element, $S_A$ is the sensitivity of the signal of the looked-for element (analyte) and $sd_{BI}$ is the standard deviation of the blank signal (background emission and interfering signal). These three quantitites can be easily measured. Equation (12) provides an estimate of the worst case. (Boumans and Vraakking in "Spectrochimica Acta 42B, 819

(1987)). The first term of the equation (12) is called the "selectivity term" and reflects, among other things, the instability of the monochromator and the effects of variations in sample composition. It is this contribution which substantially raises the detection limit and has to be eliminated either by application of high resolution spectrometers or by suitable signal-processing.

Based on static measurements, the conventional detection limit $c_{L,conv}$ is defined, which corresponds to the second term of the equation (12). Since the background emission due to the matrix solution is larger than the corresponding signal in an aqueous solution and since the relative standard deviation is relatively constant, $sd_{BI}$ and, hence, $c_{L,aq}$ are somewhat larger than the corresponding values in water which are designated by sd and c. The latter detection limit is given as a reference point for the best case estimate.

The above mentioned detection limits are equivalent to the concentration which can be determined with a relative standard deviation $rsd_A$ of 50%. At analyte concentrations near the detection limit, $sd_A$ is constant and two times $sd_A$ is constant and two time $sd_A$ equals the detection limit. Since the output of the Kalman filter is a concentration, $sd_A$ is determined from multiple measurements at these low concentrations followed by filtering. The obtained number $c_{L,Kalman}$ characterizes the complete signal-processing with the Kalman filter.

Figure 10:
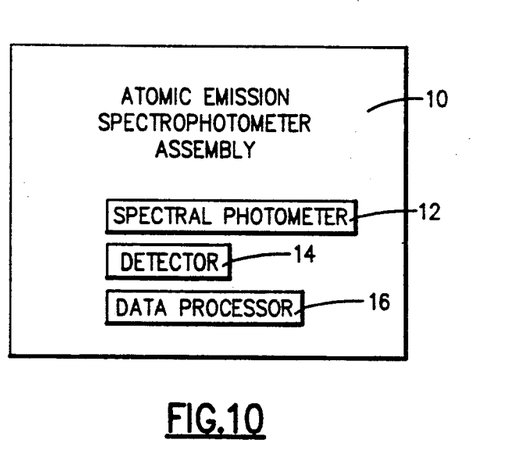
FIG. 10 is a block diagram of an atomic emission spectrophotometer assembly useful for carrying out the method of the present invention.
Figure 11:
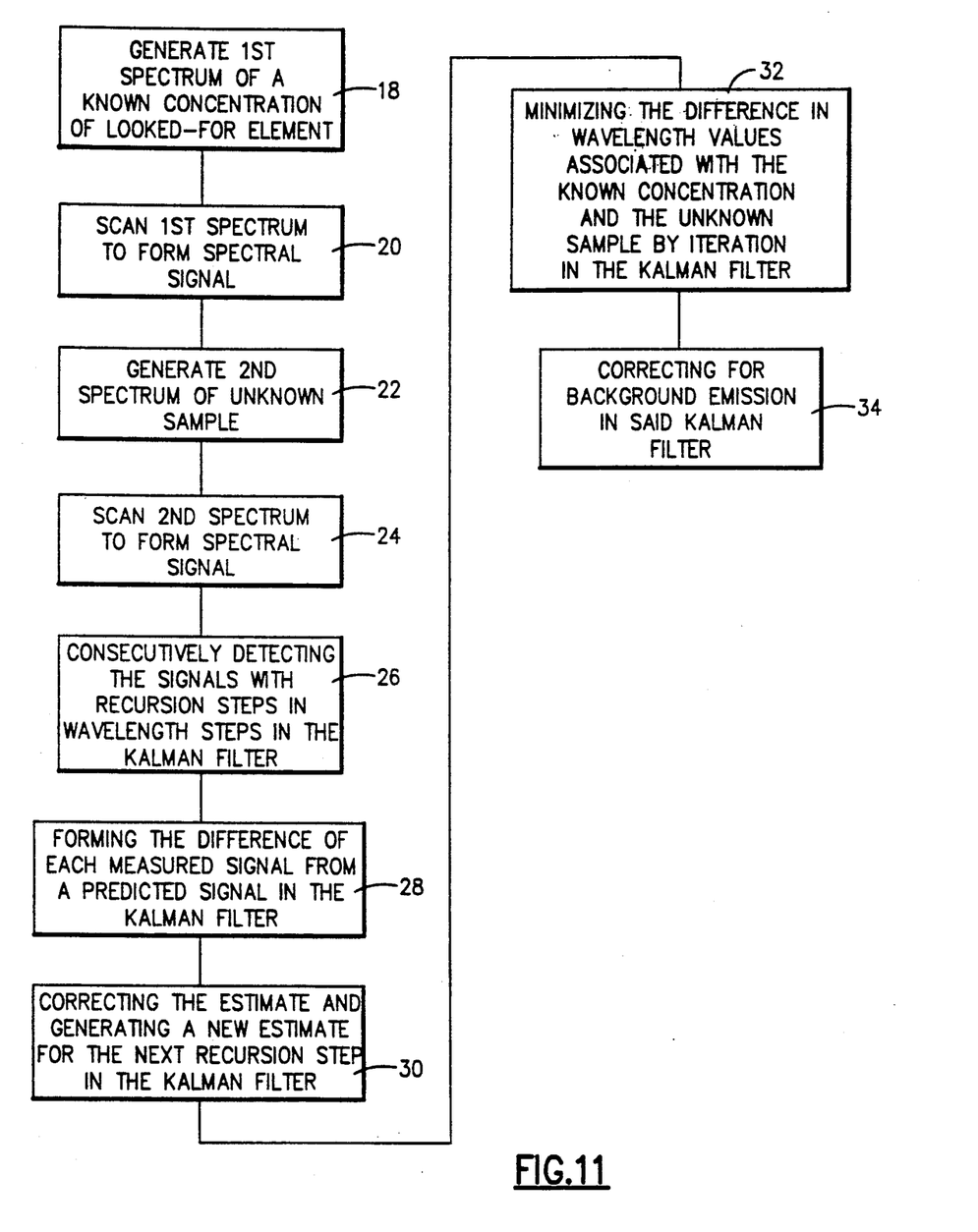
FIG. 11 is a flow chart of a method for determining concentrations in a sample by means of atomic emission spectroscopy, in accordance with the present invention.

In accordance with the present invention, an improved method for determining concentrations by means of atomic emission spectroscopy from an atomic emission spectrophotometer 10, FIG. 10, having a spectral photometer 12, a detector 14 receptive of spectra from the spectral photometer and a data processor 16 receptive of spectra data from the detector is provided. The method includes the steps of operating the atomic emission spectrophotometer 10, FIG. 10, so as to generate an atomic emission spectrum with a known concentration of a looked-for element 18, FIG. 11, and scanning the obtained emission spectrum by means of the spectral photometer 12, FIG. 10, with a spectral slit width in a wavelength range which contains a spectral line of the looked-for element to obtain a first set of spectral data 20, FIG. 11. The next step is operating the atomic emission spectrophotometer 10, FIG. 10, so as to generate an atomic emission spectrum with an unknown sample which contains the looked-for element, with the concentration of the looked-for element in the unknown sample to be determined 22, FIG. 11, and scanning the obtained emission spectrum by means of the spectral photometer 12, FIG. 10, with the same spectral slit width and in the same wavelength range in which the scanning of the emission spectrum with the known concentration was made to obtain a second set of spectral data 24, FIG. 11. The data is processed in the data processor 16, FIG. 10, which is provided by the spectral photometer 12, FIG. 10, dependent of the wavelength by means of a recursive Kalman filter to generate an estimate of the concentration of the looked-for element in the sample by consecutively detecting the signals of the spectral photometer 12 with recursion steps in wavelength steps, forming the difference of each measured signal from a predicted signal which results from an estimate of the concentration obtained in the preceding recursion step in the Kalman filter as indicated at 28, FIG. 11, and correcting the estimate of the concentration by said difference multiplied by a filter amplification for generating a new estimate for the next recursion step in the Kalman filter as indicated at 30, FIG. 11. The wavelength values associated with the signals obtained with the scanning of the emission spectrum of the known concentration, and the wavelength values associated with the signals obtained with the emission spectrum of the sample are varied relative to each other until the difference becomes independent of the wavelength and an associated difference number, which is determined by iteration, assumes a minimum value, as indicated at 32, FIG. 11, and correcting for background emission in said Kalman filter, as indicated at 34.

Figure 12:
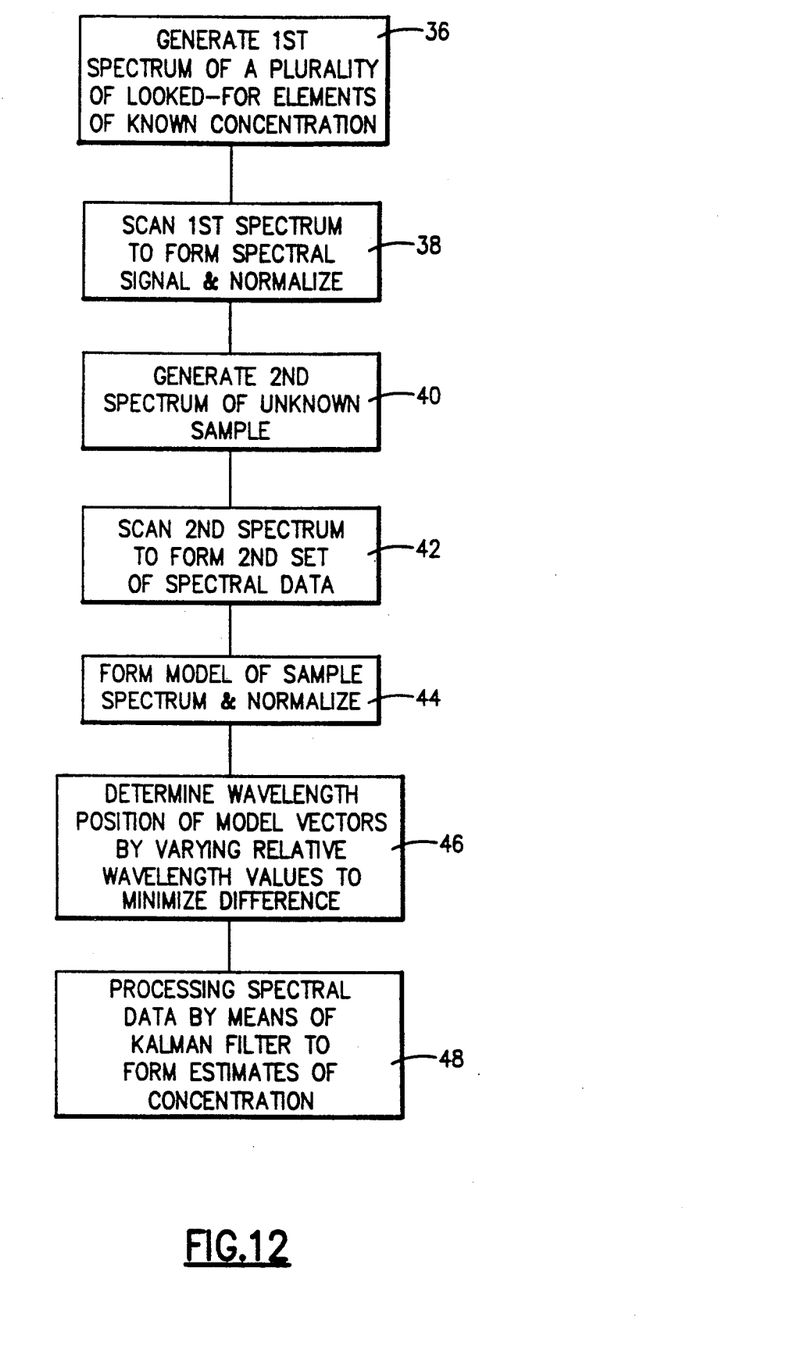
FIG. 12 is a flow chart similar to FIG. 11, but showing another embodiment of the invention.

In accordance with another form of the invention, an improved method for determining concentrations by means of atomic emission spectroscopy form the atomic emission spectrophotometer 10, FIG. 10, which includes the spectral photometer 12, the detector 14 and the data processor 16. The method includes the steps of: operating the spectrophotometer 10 so as to generate atomic emission spectra of a plurality of elements with known concentrations of the looked-for elements 36, FIG. 12, scanning the obtained emission spectra by means of the spectral photometer with a spectral slit width in a wavelength range which contains spectral lines of the looked-for elements and normalizing said spectra with respect to concentration 38, operating the atomic emission spectrophotometer 10 so as to generate an atomic emission spectrum with an unknown sample which contains the looked-for elements with the concentrations of the looked-for elements in the unknown sample to be determined 40, scanning the obtained emission spectrum by means of the spectral photometer 12 with the same spectral slit width and in the same wavelength range in which the scanning of the emission spectrum with the known concentrations were made to obtain a second set of spectral data 42, forming a model of the sample emission spectrum and normalizing said last named spectrum with respect to concentration 44, determining the relative wavelength positions of model vectors in the emission spectrum model by varying relative to each other known emission wavelength values of the individual elements and the measured emission wavelength values until the difference becomes independent of the wavelength and the associated difference number which is determined by iteration approaches a minimum value 46, and processing in said data processor 16 the spectral data which is provided dependent of the wavelength by means of a recursive Kalman filter to form concentration estimates according to the model emission spectrum 48, FIG. 12. In one form of the invention the emission lines of the looked-for elements overlap within the scanned wavelength range. Experimentally, the following was found:

The measurements were performed with a Perkin-Elmer Plasma II-system equipped with a one-meter Ebert monochromator. The monochromator of a medium resolution has a holographic grating with 1800 lines per millimeter, resulting in a reciprocal linear dispersion of 0.527 nm/mm. The practical resulution has been measured to be about 17 pm. A value of 15-20 pm usually applies to monochromators in ICP-AES systems. With such a system there is a reasonable chance that emission lines suffer from spectral interferences and, hence, that the selectivity term dominates. Moreover, the observed interferences are examples of the worst case. Many problems dealing with these interferences may arise simultaneously. These problems may be, for example: small line separation with approximately one order of magnitude lower than the practical resolution, equal shapes of the spectral lines due to dominant contribution of the instrument function to the total line profile, or low intensity of the spectral line with respect to the interfering intensities.

The spectral window was set to 128 pm in the majority of the experiments, the overlapping feature showing up in the centre. The step size was about 1.5 pm. The integration time was adjusted to 0.1 second per step. So, one spectral scan took about 8.5 seconds.

The experimental models can be determined in different ways. In a series of samples the analyte is present up to a certain concentration level. A solution of the pure analyte at that level is prepared. This solution is measured ten times by scanning the spectrum. The positions of the peak maximum in the ten scans is determined by a peak search procedure. Then, the scans are shifted relative to a wavelength division so that the peak maxima coincide. Then, the average intensity or sensitivity is calculated in each point of the scan together with the standard deviation in the sensitivity at the peak maximum.

One scan per solution of the pure interfering elements is sufficient since the shape, not the intensity, of the emission is important. In signal processing with a Kalman filter an inaccurate intensity of an element of the model affects only the concentration estimate of that one element. However, when, preferably, the models of the interfering elements are determined in the same way as described above for the analyte, the Kalman filter simultaneously performs a multi-component analysis.

As an example of the described method five samples have been analyzed: neodym (Nd) in praseodym (Pr), phosphorus (P) in copper (Cu), cadmium (Cd) in iron (Fe), indium (In) in molybdenum (Mo) and wolfram (W), and mangan (Mn). The signal-processing by means of the Kalman filter will be completely described with the example of neodym in a matrix of praseodym.

Figure 2:
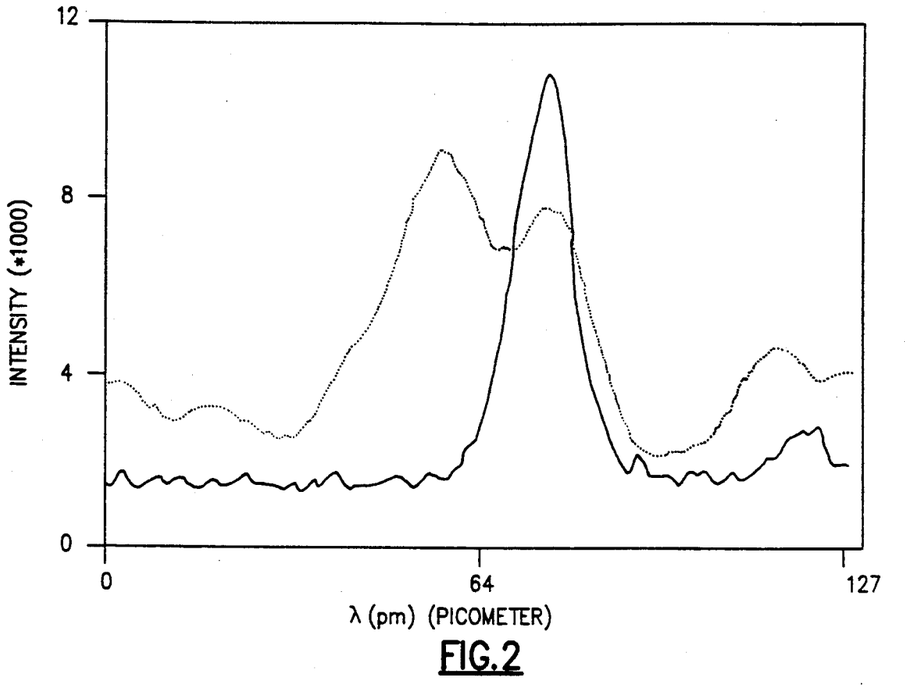
FIG. 2 shows the scanning of a spectral window of 128 picometers with the spectral line Nd 11 of 401.225 nm for a solution of neodym having a concentration of 508 micrograms per liter, as well as for a solution of praseodym having a concentration of 99.1 milligrams per liter.

All six prominent spectral lines of neodym suffer from strong interferences due to the emission spectral lines of praseodym at a concentration level of 100 milligrams per liter. The Nd II spectral line of 401.225 nm is the most prominent spectral line in an aqueous solution. FIG. 2 shows scans for aqueous solutions of 508 micrograms per liter neodym and 99.1 milligrams per liter praseodym in the spectral window of the spectral line Nd II of 401.225 nm. The neodym spectral line is interfered by a praseodym spectral line approximately 2 picometers (pm) to the right and a praseodym spectral line approximately 17 pm to the left of the emission spectral line of neodym. Since the relative peak positions are not accurately known from the literature, the separation for the strongest spectral lines in both scans has been determined to be 17.2 pm by signal processing with the Kalman filter. Based on the data which were obtained from the scan, "true", "conventional" and "aqueous" detection limits have been determined, as presented in Table 1.

The experimental models have been determined from scans similar to the scans displayed in FIG. 2. The intensities have been divided by corresponding concentration values. Then, ten consecutive scans from each of five samples were made and were filtered by signal processing with a Kalman filter. From this, concentrations resulted which are listed in Table 2. Table 2 also lists the standard deviations $sd_A$ which resulted with the filtered concentrations. From the $sd_A$ values the detection limit $c_{L,Kalman}$ has been calculated to be 9.7 micrograms per liter.

This value compares very favorably with the other values of the detection limit listed in Table 1. It is fifteen times lower than the "true" detection limit. Moreover, it is even lower than the "conventional" and the "aqueous" detection limit. This can be understood by the fact that, due to the iteration based on the "innovations", the selectivity term was eliminated and that, due to the filtering, the noise has been averaged.

Figure 3:
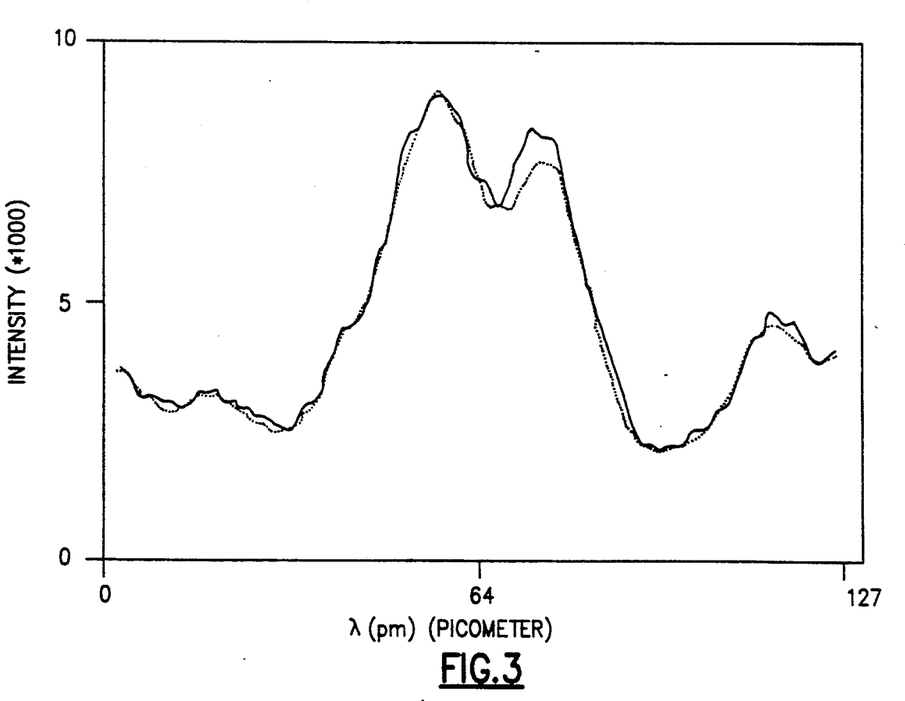
FIG. 3 shows, in a spectral window of 128 picometers with the spectral line Nd 11 of 401.225 nm, the sample—and matrix spectrum of a concentration of 29.7 micrograms per liter neodym in a solution having a concentration of 99.1 milligrams per liter praseodym for the experimentally achieved scan of the sample as well as for the matrix spectrum as it was calculated from the filtered praseodym concentration and the background.
Figure 4:
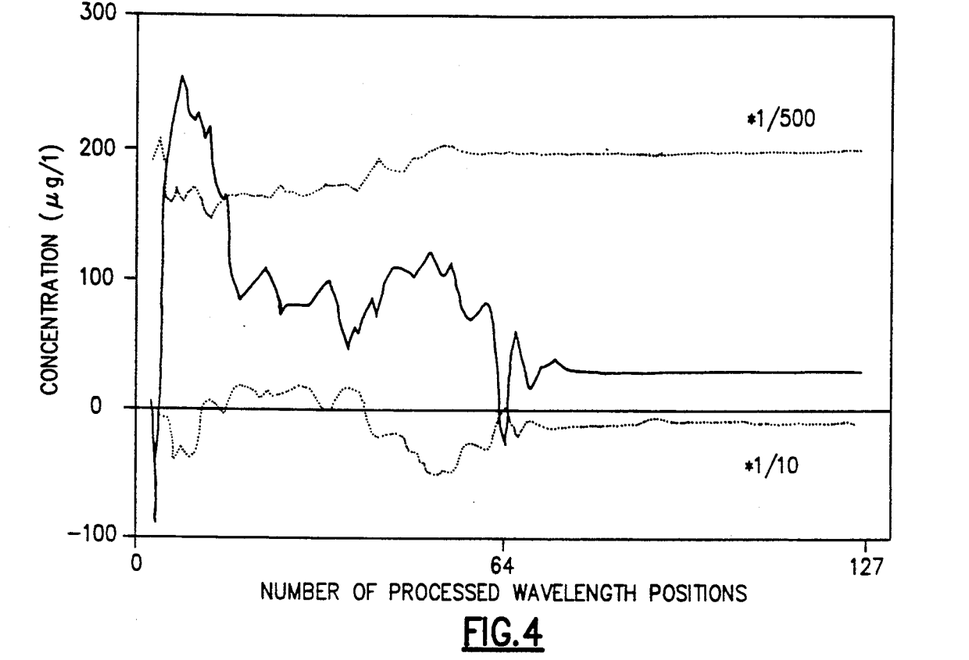
FIG. 4 shows concentration estimates and the background as a function of the wavelength positions which were processed in the spectral window around the spectral line Nd 11 of 401.225 nm for a solution having a concentration of 29.7 micrograms per liter neodym in a solution of 99.1 milligrams per liter praseodym.

For demonstrating the performance of the Kalman filter, FIG. 3 shows a scan of 29.7 micrograms per liter neodym in 99.1 milligrams per liter praseodym. From this, neodym can be determined with a precision of 16%. Prasodym is determined with a precision of 11.1%. The intensity of the spectral line of neodym is only one-tenth of the intensity of the spectral line of praseodym. In FIG. 4 the estimates of the concentrations and of the background emission, recursively calculated from the scan are displayed as a function of the number of wavelength positions processed. From these curves it is clear that, as soon as the emission signal of one of the elements comes up (see FIG. 2), the corresponding concentration is immediately properly estimated.

Figure 5:
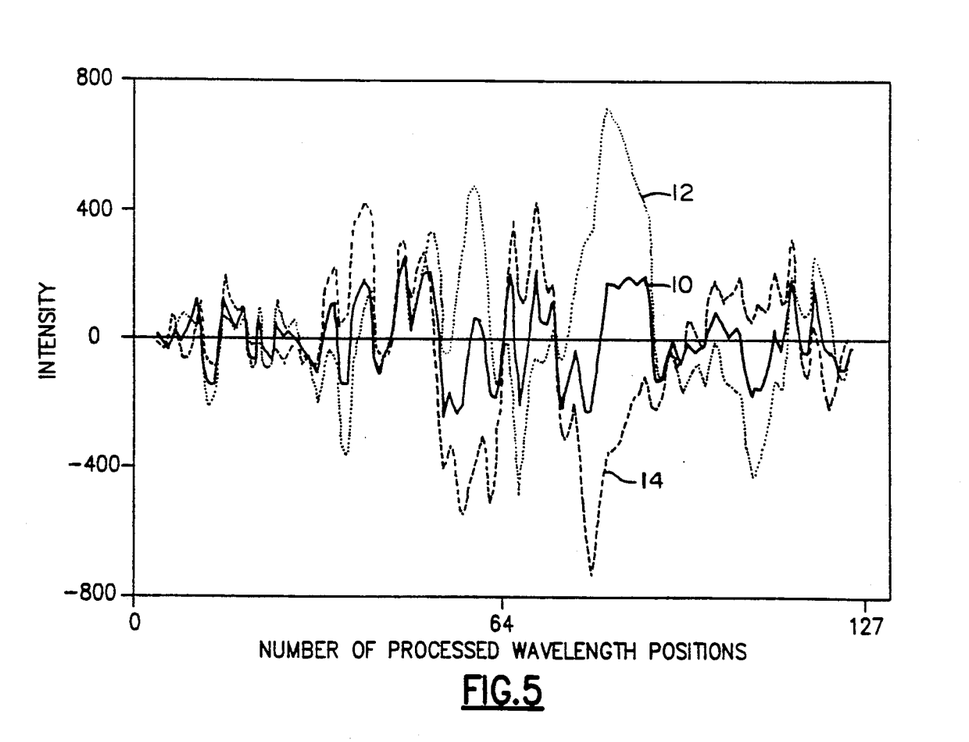
FIG. 5 shows the course of the "innovation", i.e. the difference between the measured and the precalculated intensity in the spectral window of the spectral line Nd 11 of 401.225 nm for a concentration of 29.7 micrograms per liter neodym in a solution of 99.1 milligrams per liter prasedym: when the wavelength scales for the measurement and the model coincide, when the wavelength scale of the measurement is shifted by +1 pm (picometer) relative to the wavelength scale of the models and, finally, when the wavelength scale of the measurement is shifted by −1 pm relative to the models.

The influence of shifted peak positions upon accuracy is illustrated in Table 3. Starting from a situation where the measured spectrum and models are at their proper wavelength positions, $\Delta\lambda$ denotes the shift of the scan with respect to the models. $\delta\lambda$ denotes the shift of two models with respect to each other, i.e. of scanned emission spectra of the single elements. For a shift $\Delta\lambda = +/-1$ pm a bias of the neodym concentation of 50% results. In FIG. 5 numeral 10, solid line, designates the innovation as a function of the wavelength positions processed, if the measurement and model vectors are in proper position. Numeral 12, dotted line, designates the corresponding graph with the measurement scale shifted by +1 pm with respect to the model vectors. Numeral 14, dashed line, designates the graph with the scale of the measurement shifted by −1 pm with respect to the model vectors. That is, FIG. 5 displays the corresponding course of the innovation sequences, i.e. the course when the scan of the sample is in the proper wavelength position relative to the models, and when the scan is shifted by +1 pm or −1 pm with respect to the models. The thick, full line shows the course of the innovation when the scan of the sample and the model are in the proper wavelength position. The dotted line shows the course of the innovation when the scan is shifted by +1 pm with respect to the models. The broken line shows the course of the innovation when the scan is shifted by −1 pm with respect to the models. The dotted line shows a bias to the positive side while the broken line shows a bias to the negative side. It is obvious that the course of the "innovation" provides a criterion for the relative shift of the spectra: this criterion can be used to eliminate the errors caused by the optical instability of the monochromator.

When the models are shifted by 1 pm from their proper position ($\alpha\lambda = +/-1$ pm), according to Table 3, the bias in the concentration of neodym is 3%. This value is quite small. However, some structures are still present in the course of the innovation, indicating the error in the models. At higher concentrations, e.g. 392 micrograms per liter neodym, the bias of the estimates is smaller and amounts to 5% with $\Delta\lambda = +/-1$ pm and to 1% with $\delta\lambda = +/-1$ pm.

The detection limits in all samples studied are presented in Table 1. As expected, the order of the detection limits is $c_{L,true} > c_{L,conv} > c_{L,aq}$. However, the most striking conclusion is that $c_{L,Kalman}$ is substantially lower than the conventional and the "aqueous" detection limits. Table 2 shows some examples of the accuracy of the analytical results obtained with the Kalman filter. It turns out that the Kalman filter yields exact results. At high matrix concentrations (praseodym and molybdenum/wolfram), a matrix effect is present. Table 3 gives an illustration of the bias in some concentration estimates if one is not able to eliminate the effect of the drift of the spectral window.

Next some examples will be described which illustrate the effect of the signal-generating and signal processing for different possible situations.

The effect of signal-processing by means of the Kalman filter at overlapping peaks with large separation will be demonstrated with phosphorus (P) in a matrix of copper (Cu).

Phosphorus has only two prominent spectral lines at the wavelength 213.618 nm and at the wavelength 214.914 nm. These spectral lines are both interfered by copper signals. For the next two spectral lines of phosphorus the detection limits are four to five times higher. These spectral lines are also interfered by copper. So, it is hard to determine phosphorus at low levels in matrices containing copper.

Solutions of 300 to 1000 micrograms per liter phosphorus in a matrix of 20 milligrams per liter copper were studied in a spectral window at 213.618 nm.

Since the weak phosphorus signal lies on the edge of the copper signal which is very intense, the wavelength position of the scan with respect to the wavelength position of the model is crucial. A shift $\Delta\lambda$ of $+/-0.1$ pm causes a bias of 30% in the phosphorus concentration obtained (Table 3). As stated, such a bias of the wavelength positions is eliminated by the criterion of the flat course of the innovations. Also, the wavelength difference of the two model peaks is rather critical. With a shift of $\delta\lambda = +/-1$ pm the bias in the phosphorus concentration estimates may be as high as 10%. This explains the requirement for knowing the relative wavelength positions of peak maxima up to an accuracy of at least 0.1 pm. According to the literature the separation between the peak maxima of copper and phosphorus is about 20 pm. Therefore, an accurate value is badly needed for the separation. A search for a flat course of the innovation yields the value of 20.1 pm.

Figure 6:
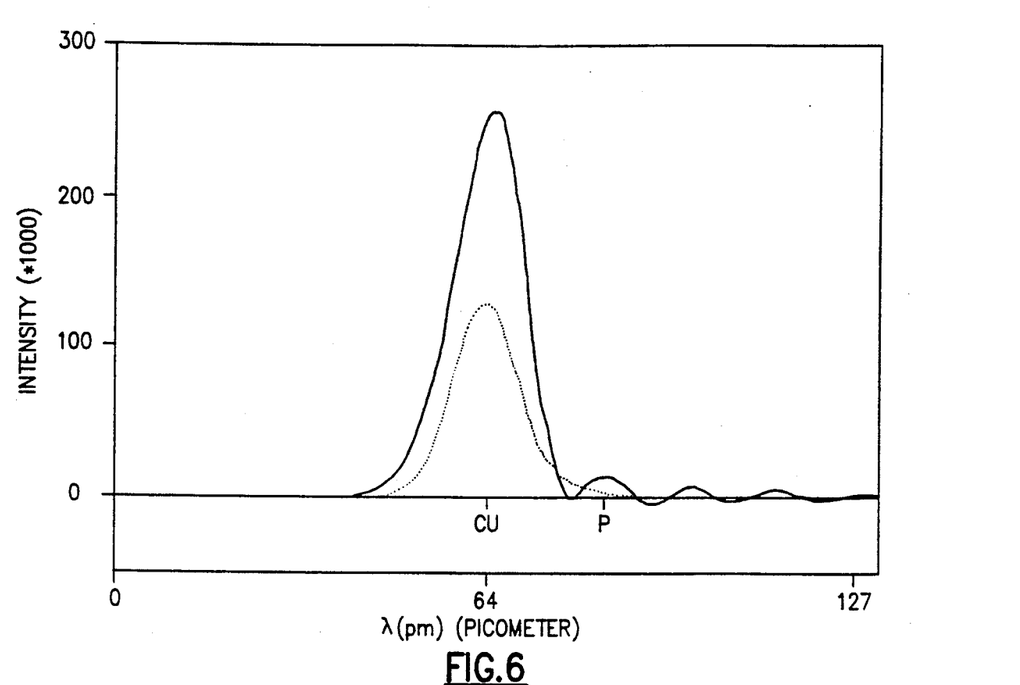
FIG. 6 illustrates the effect of a Fourier deconvolution in a spectral window with the spectral line P I of 213.618 nm for the experimental scan of the emission spectrum of 1.03 milligrams per liter phosphorus in a solution of 19.8 milligrams per liter copper as well as for the deconvoluted spectrum.

With this line separation and a practical resolution of 17 pm, the line pair can be Fourier deconvoluted for instrumental broadening. The result of this Fourier deconvolution is shown in FIG. 6. Side-lobes are generated upon deconvolution even when an integration time of one second is applied during the measurement. Since the side-lobe amplitude depends upon the noise in the scan, it is difficult to determine its intensity at the position of the phosphorus line and the detection limit will worsen. Though the limit will be better than the "true" limit, it is higher than $c_{L,Kalman}$. The detection limit with the method of the Fourier deconvolution is about 400 micrograms per liter. So, the application of the Fourier deconvolution is limited through the scan and the detection limit. This method can only be applied for a line separation in the order of the resolution of the spectrometer. The Fourier deconvolution is independent of the sample composition. However, if the interfering elements are known, signal-processing by the Kalman filter is preferred over Fourier deconvolution.

A second example is the analysis of elements with overlapping spectral lines at small line separation.

Figure 7:
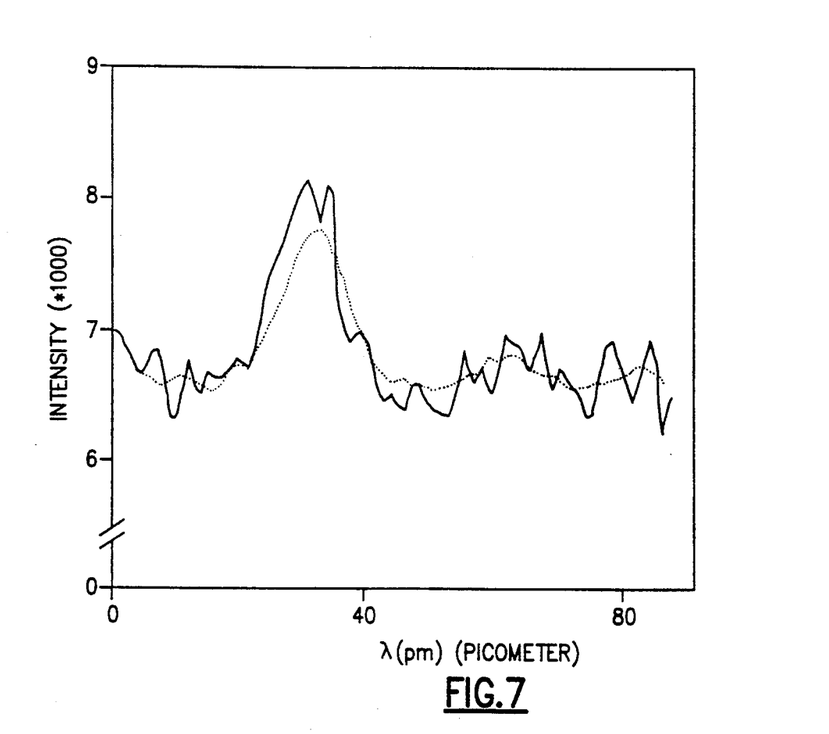
FIG. 7 shows the sample—and the matrix spectrum, in an 88 picometer wide spectral window with the spectral line Cd 11 226.502, for the experimental scan of the emission spectrum of a sample with 18.9 micrograms per liter cadmium in a solution having 607 milligrams per liter iron, as well as for the matrix spectrum as it was calculated from the filtered iron concentration and the background.

A system has been investigated in which the peak separation is small and the concentrations have simultaneously to be determined from one spectral feature. The investigated system contains the spectral lines Cd 11 of cadmium at 226.502 nm, interfered by a spectral line of iron at 226.505 nm. The line separation between these two spectral lines is 3.3 pm. At a spectral bandwidth of the spectral photometer of 17 pm, the two spectral lines have an identical shape. Moreover, with an iron solution of 600 milligrams per liter the cadmium signal near the detection limit is smaller by the factor of five than the iron signals illustrated in FIG. 7. Table 2 shows that, even under unfavorable circumstances, $c_{L,Kalman}$ is substantially lower than the other detection limits.

Figure 8:
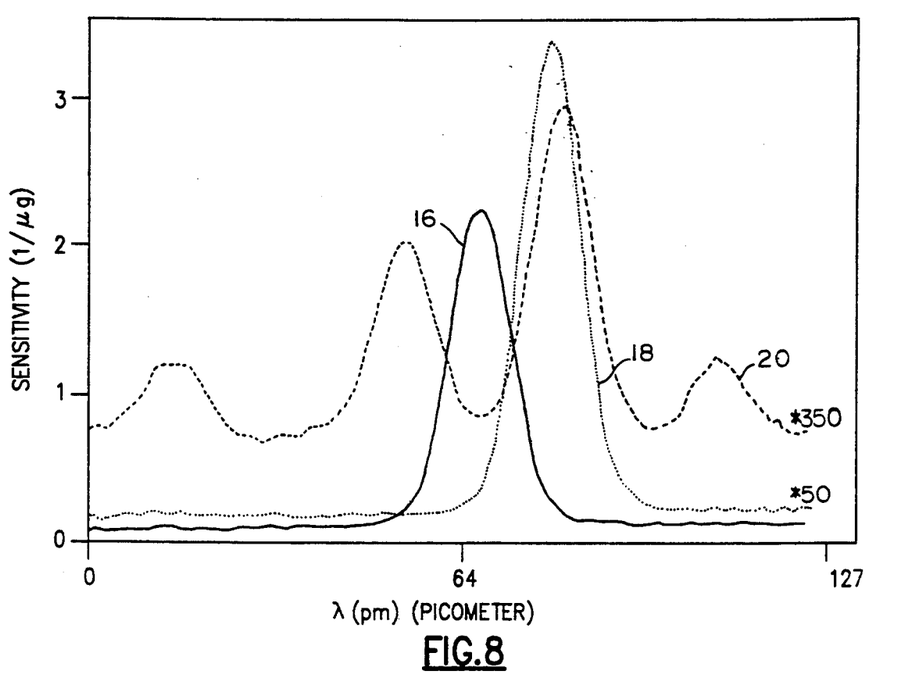
FIG. 8 shows experimental models in a 128 pm wide spectral window with the spectral line In I of 325.607 nm, i.e. for indium, molybdenum and wolfram.
Figure 9:
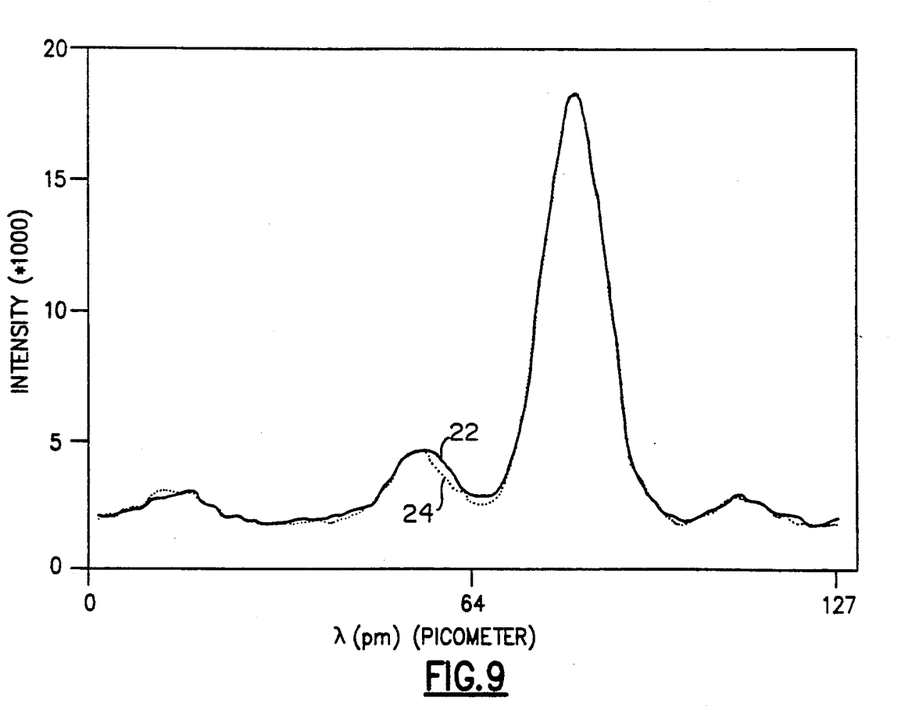
FIG. 9 shows the matrix spectrum which was calculated from the filtered molybdenum and wolfram concentrations.

Next, the performance of the Kalman filter in the presence of more than one interfering component will be investigated. Heretofore, a system with indium, molydaneum and wolfram was used. Actually, this system is treated with a constant background emission as a four-component system. FIG. 8 shows, as a function of wavelength, experimental models in the 128 pm wide spectral window of indium at 325.609 nm. In FIG. 8 the solid line 16 is the graph for indium, the dotted line 18 is the graph for molybdenum and the dashed line 20 is the graph for tungsten. That is, FIG. 8 shows the scanned spectra which serve as experimental models. With respect to the emission spectral lines of indium at 325.609 nm molydaneum and wolfram show maximal emission intensities in the spectral windows at relative wavelength positions of $+12.0$ pm and $+14.0$ pm, respectively. Applying the criterion of the flat course of the innovation, the wavelength positions were found to be $+11.5$ pm and 13.5 pm, respectively. The indium concentration was varied from 200 to 800 micrograms per liter in a solution containing 200 milligrams per liter molydaneum and 800 milligrams per liter wolfram (FIG. 9). That is, FIG. 9 shows the sample and matrix spectrum in the same spectral window as in FIG. 8. The solid line 22 shows the experimental scan of 198 $\mu g/l$ indium in a 200 mg/l molybdenum and 798 mg tungsten solution. The dotted line 24 is the matrix spectrum calculated from the filtered molybdenum and tungsten concentration level.

The application of the Kalman filter led to a detection limit which is eight times lower than the "true" detection limit $c_{L,true}$ (Table 1). Again, not only was the selectivity term eliminated but noise averaging is also substantial. Since the selectivity term does not play a role any more, the line selection seems to become almost independent of the matrix composition.

The described signal processing by a Kalman filter can also feasibly be applied for scanning single spectral lines. This is illustrated by the spectral line Mn II of mangan at 257.610 nm. The experimental model was determined at a concentration of 100 micrograms per liter. Scans for mangan in concentrations from 5 to 40 microgramms per liter were made. Table 1 shows that indeed the Kalman filter allows for noise averaging with a factor of about two.

TABLE 1

| Emission Spectral Line (nm) | Matrix | Detection Limits ($\mu g/L$) | | | |
| --- | --- | --- | --- | --- | --- |
| | | $c_{L,Kalman}$ | $c_{L,true}$ | $c_{L,conv}^a$ | $c_{L,aq}^a$ |
| Nd II 401.225 | 100 mg/L Pr | 9.7 | 150 | 24 | 14 |

TABLE 1-continued

| Emission Spectral Line (nm) | Matrix | Detection Limits (μg/L) | | | |
|---|---|---|---|---|---|
| | | $c_{L,Kalman}$ | $c_{L,true}$ | $c_{L,conv}^a$ | $c_{L,aq}^a$ |
| P I 213.618 | 20 mg/L Cu | 240 | 630 | 290 | 320 |
| Cd II 226.502 | 600 mg/L Fe | 9.5 | 43 | 22 | 17 |
| In I 325.609 | 200 mg/L Mo 800 mg/L W | 46 | 360 | 170 | 110 |
| Mn II 257.610 | — | 1.2 | — | — | 2.2 |

TABLE 2

Accuracy of the analytical results achieved using a Kalman filter for signal processing

| Analyt | | | Matrix | |
|---|---|---|---|---|
| prepared | Kalman-Filter | $sd_A$ | prepared | Kalman-Filter |
| Nd (μg/L) | | | Pr (mg/L) | |
| 29.7 | 27.8 | 5.0 | 99.1 | 97.3 |
| 60.7 | 54.2 | 4.9 | 99.9 | 98.9 |
| 102 | 98.2 | 6.3 | 100 | 99.1 |
| 199 | 193 | 3.4 | 99.5 | 98.5 |
| 403 | 392 | 4.6 | 100 | 100.4 |
| P (μg/L) | | | Cu (mg/L) | |
| 348 | 281 | 120 | 20.2 | 20.2 |
| 490 | 513 | 122 | 20.3 | 20.3 |
| 1030 | 1090 | 118 | 19.8 | 19.8 |
| In (μg/L) | | | Mo/W (mg/L) | |
| 198 | 165 | 19 | 200/798 | 195/786 |
| 421 | 359 | 25 | 199/797 | 194/787 |
| 627 | 548 | 25 | 199/795 | 192/784 |
| 821 | 694 | 22 | 199/793 | 193/785 |

TABLE 3

Influence of the shift of the peak position in the measured spectrum and the models on the accuracy of the estimates for the concentrations

| $\Delta\lambda^a$ (pm) | $\delta\lambda^a$ (pm) | Nd (μg/L) | Deviation (%) | P (μg/L) | Deviation (%) | Mn (μg/L) | Deviation (%) |
|---|---|---|---|---|---|---|---|
| 0 | 0 | 27.8 | — | 513 | — | 5.21 | — |
| 1 | — | 41.6 | 50 | | | 5.02 | 3.6 |
| −1 | — | 13.5 | 51 | | | 5.30 | 1.7 |
| 0.1 | — | | | 664 | 29 | | |
| −0.1 | — | | | 363 | 29 | | |
| — | 1 | 27.0 | 2.9 | 561 | 9.4 | | |
| — | −1 | 27.6 | 0.7 | 497 | 3.1 | | |

Although a certain particular embodiment of the invention is herein disclosed for purposes of explanation, further modification thereof, after study of this specification, will be apparent to those skilled in the art to which the invention pertains. Reference should accordingly be had to the appended claims in determining the scope of the invention.

What is claimed is:

1. Method for determining concentrations by means of atomic emission spectroscopy from an atomic emission spectrophotometer having a spectral photometer, a detector receptive of spectra from the spectral photometer and a data processor receptive of spectra data from the detector, the method comprising the steps of:

(a) operating the atomic emission spectrophotometer so as to generate an atomic emission spectrum with a known concentration of a looked-for element, (b) scanning the obtained emission spectrum by means of the spectral photometer with a spectral slit width in a wavelength range which contains a spectral line of the looked-for element to obtain a first set of spectral data, (c) operating the atomic emission spectrophotometer so as to generate an atomic emission spectrum with an unknown sample which contains the looked-for element in the unknown sample to be determined, (d) scanning the obtained emission spectrum by means of the spectral photometer with the same spectral slit width and in the same wavelength range in which the scanning of the emission spectrum with the known concentration was made to obtain a second set of spectral data, (e) processing in said data processor the spectral data, which is provided by the spectral photometer dependent of the wavelength by means of a recursive Kalman filter to generate an estimate of the concentration of the looked-for element in the sample, (f) consecutively detecting with said recursive Kalman filter the signals of the spectral photometer with recursion steps in wavelength steps, (g) forming with said recursive Kalman filter the difference of each measured signal from a predicted signal which results from the estimate of the concentration obtained in the preceding recursion step, and (h) correcting with said recursive Kalman filter the estimate of the concentration by said difference multiplied by a filter amplification for generating a new estimate for the next recursion step.

2. The method as set forth in claim 1 wherein the wavelength values associated with the signals obtained with the scanning of the emission spectrum of the known concentration, and the wavelength values associated with the signals obtained with the emission spectrum of the sample are varied relative to each other until the difference becomes independent of the wavelength and an associated difference number, which is determined by iteration, assumes a minimum value.

3. Method for determining concentrations by means of atomic emission spectroscopy from an atomic emission spectrophotometer having a spectral photometer, a detector receptive of spectra from the spectral photometer and a data processor receptive of spectra data from the detector, the method comprising the steps of:

(a) operating the spectrophotometer so as to generate atomic emission spectra of a plurality of elements with known concentrations of the looked-for elements, (b) scanning the obtained emission spectra by means of the spectral photometer with a spectral slit width in a wavelength range which contains spectral lines of the looked-for elements and normalizing said spectra with respect to concentration, (c) operating the atomic emission spectrophotometer so as to generate an atomic emission spectrum with an unknown sample which contains the looked-for elements with the concentrations of the looked-for element in the unknown sample to be determined.

(d) scanning the obtained emission spectrum by means of the spectral photometer with the same spectral slit width and in the same wavelength range in which the scanning of the emission spectrum with the known concentration were made to obtain a second set of spectral data, (e) forming a model of the sample emission spectrum and normalizing said last named spectrum with respect to concentration, (f) determining the relative wavelength positions of model vectors in the emission spectrum model by varying relative to each other known emission wavelength values of the individual elements and the measured emission wavelength values until the difference becomes independent of the wavelength and the associated difference number which is determined by iteration approaches a minimum value, and (g) processing in said data processor the spectral data which is provided dependent of the wavelength by means of a recursive Kalman filter to form concentration estimates according to the model emission spectrum.

4. The method as set forth in claim 3, wherein the emission lines of the looked-for elements overlap within the scanned wavelength range.

* * * * *